United States Patent [19]

Serban et al.

[11] Patent Number: 4,738,710

[45] Date of Patent: * Apr. 19, 1988

[54] HERBICIDAL ALKANE CARBOXYLIC ACID DERIVATIVES

[75] Inventors: Alexander Serban, Doncaster; Keith G. Watson, Box Hill North, both of Australia

[73] Assignee: ICI Australia Limited, Melbourne, Australia

[*] Notice: The portion of the term of this patent subsequent to Apr. 24, 2001 has been disclaimed.

[21] Appl. No.: 780,716

[22] Filed: Sep. 27, 1985

Related U.S. Application Data

[63] Continuation of Ser. No. 361,605, Mar. 25, 1982, abandoned, which is a continuation-in-part of Ser. No. 201,979, Oct. 29, 1980, Pat. No. 4,444,584.

[30] Foreign Application Priority Data

Nov. 19, 1979 [AU] Australia ............................. PE1379
Nov. 20, 1979 [AU] Australia ............................. PE1398
Apr. 2, 1981 [AU] Australia ............................. PE8265

[51] Int. Cl.$^4$ .................... A01N 43/42; C07D 215/20
[52] U.S. Cl. ......................................... 71/94; 546/153
[58] Field of Search ............................. 546/153; 71/94

[56] References Cited

U.S. PATENT DOCUMENTS

| | | | |
|---|---|---|---|
| 3,965,109 | 6/1976 | Tomlin et al. ................. | 71/94 X |
| 4,063,928 | 12/1977 | Johnston ..................... | 71/94 |
| 4,105,435 | 8/1978 | Nishiyama et al. ............. | 71/94 |
| 4,236,912 | 12/1980 | Johnston et al. .............. | 71/94 |
| 4,259,105 | 3/1981 | Maeda et al. ................. | 71/108 |
| 4,314,065 | 2/1982 | Serban et al. ................ | 548/222 |
| 4,444,584 | 4/1984 | Serban . | |

FOREIGN PATENT DOCUMENTS

| | | |
|---|---|---|
| 0881815 | 8/1980 | Belgium . |
| 0029319 | 5/1981 | European Pat. Off. . |
| 2047882 | 3/1971 | France . |
| 0012379 | 1/1979 | Japan . |
| 0143970 | 11/1980 | Japan ................... 71/94 |
| 2042539 | 9/1980 | United Kingdom ........ 71/94 |

OTHER PUBLICATIONS

Ciba-Geigy A.-G., Chemical Abstracts, vol. 90, 181588z (06/04/79).

*Primary Examiner*—Donald G. Daus
*Assistant Examiner*—Diana G. Rivers
*Attorney, Agent, or Firm*—Cushman, Darby & Cushman

[57] ABSTRACT

The invention concerns novel compounds of the formula I wherein:

A, B, D, E, $J^1$, $J^2$, U and V are chosen from hydrogen, halogen, nitro, cyano, thiocyano, amino, substituted amino, alkyl, substituted alkyl, alkenyl, cycloalkyl, alkoxy, substituted alkoxy, alkylthio, alkylsulfinyl, substituted alkylsulfinyl, alkylsulfonyl, substituted alkylsulfonyl, sulfamoyl, substituted sulfamoyl, sulfo, carboxy, alkoxycarbonyl, carbamoyl, substituted carbamoyl and optionally substituted phenyl, phenoxy and phenylthio;

$R^1$ is chosen from hydrogen, alkyl, substituted alkyl, alkenyl, alkanoyl and alkoxycarbonyl; $R^2$ is chosen from hydrogen, alkyl, substituted alkyl and alkenyl; or $R^1$ and $R^2$ together form an alkylidene group;

W is chosen from cyano, thiocarbamoyl, the group —CH$_2$Z wherein Z is chosen from halogen, hydroxy, mercapto, alkoxy, haloalkoxy, alkylthio and optionally substituted amino, and the group $$-\overset{\overset{\displaystyle O}{\|}}{C}-G$$

which may be a carboxylic acid group or a derivative thereof such as an acid salt, acid ester, acid amide, acid sulfonamide or acid oxime ester;

X is chosen from oxygen and sulfur;

Y is chosen from oxygen sulfur and optionally substituted imino;

$\phi$ is chosen from oxygen and RAn wherein R is alkyl or benzyl and An is an anion;

k is 0 or 1; and n is 0, 1 or 2.

The compounds are herbicides and in further embodiments the invention provides herbicidal compositions containing as active ingredient a compound of formula I and a process for severely damaging or killing unwanted plants by applying to the plants or to the growth medium of the plants an effective amount of a compound of formula I.

9 Claims, No Drawings

HERBICIDAL ALKANE CARBOXYLIC ACID DERIVATIVES

This is a continuation of application Ser. No. 361,605, filed Mar. 25, 1982 and now abandoned, which is a continuation-in-part of application Ser. No. 201,979, filed Oct. 29, 1980, now U.S. Pat. No. 4,444,584.

This invention relates to organic compounds having biological activity and in particular to organic compounds having herbicidal properties, to processes for the preparation of such compounds, to intermediates useful in the preparation of such compounds and to herbicidal compositions and processes utilizing such compounds.

We have now found a new class of quinolines which exhibit biological activity, and in particular herbicidal activity.

Accordingly the invention provides a compound of formula I:

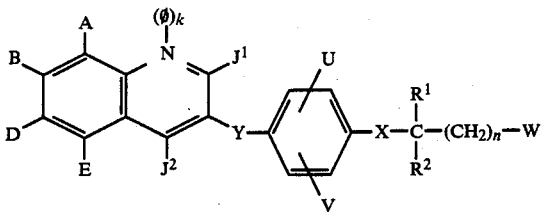

or a salt thereof wherein:

A, B, D, E, $J^1$, $J^2$ U and V are independently chosen from the group consisting of hydrogen, halogen, nitro, cyano, thiocyano, amino, $C_1$ to $C_6$ alkylamino, di($C_1$ to $C_6$ alkyl)amino, $C_1$ to $C_6$ alkyl, $C_1$ to $C_6$ haloalkyl, $C_2$ to $C_6$ alkenyl, $C_3$ to $C_7$ cycloalkyl, $C_1$ to $C_6$ alkoxy, $C_1$ to $C_6$ haloalkoxy, $C_1$ to $C_6$ alkylthio, $C_1$ to $C_6$ alkylsulfinyl, $C_1$ to $C_6$ alkylsulfonyl, $C_1$ to $C_6$ haloalkylsulfinyl, $C_1$ to $C_6$ haloalkylsulfonyl, sulfo, $C_1$ to $C_6$ alkoxysulfonyl, sulfamoyl, N-($C_1$ to $C_6$ alkyl)sulfamoyl, N,N-di($C_1$ to $C_6$ alkyl)sulfamoyl, carboxy, ($C_1$ to $C_6$ alkoxy)carbonyl, carbamoyl, N-($C_1$ to $C_6$ alkyl)carbamoyl, N,N-di($C_1$ to $C_6$ alkyl)carbamoyl, phenyl, phenoxy, phenylthio, and the groups substituted phenyl, substituted phenoxy and substituted phenylthio wherein in each group the phenyl ring is substituted with from 1 to 3 substituents chosen from the group consisting of halogen, $C_1$ to $C_6$ alkyl, $C_1$ to $C_6$ haloalkyl, $C_1$ to $C_6$ alkoxy, nitro and cyano;

$R^1$ is chosen from the group consisting of hydrogen, $C_1$ to $C_6$ alkyl, $C_2$ to $C_6$ alkenyl, $C_2$ to $C_6$ alkoxyalkyl, $C_1$ to $C_6$ haloalkyl, acetyl, propionyl and $C_2$ to $C_6$ alkoxycarbonyl, $R^2$ is chosen from the group consisting of hydrogen, $C_1$ to $C_6$ alkyl, $C_2$ to $C_6$ alkenyl, $C_2$ to $C_6$ alkoxyalkyl and $C_1$ to $C_6$ haloalkyl, or $R^1$ and $R^2$ together may form a methylene, ethylidene, propylidene or isopropylidene group;

W is chosen from the group consisting of cyano, thiocarbamoyl,

and $CH_2Z$ wherein: G is chosen from the group consisting of hydroxy, mercapto, $C_1$ to $C_{10}$ alkoxy, $C_1$ to $C_{10}$ haloalkoxy, $C_2$ to $C_{10}$ alkenyloxy, $C_2$ to $C_{10}$ alkynyloxy, $C_1$ to $C_{10}$ alkylthio, $C_2$ to $C_{10}$ alkenylthio, $C_2$ to $C_{10}$ alkynylthio, $C_3$ to $C_7$ cycloalkoxy, $C_3$ to $C_7$ cycloalkoxy substituted with 1 or 2 $C_1$ to $C_4$ alkyl groups, phenoxy, phenylthio, benzyloxy, benzylthio, the group $C_1$ to $C_{10}$ alkoxy substituted with a substituent chosen from the group consisting of $C_1$ to $C_6$ alkoxy, amino, ammonio, cyano, N-($C_1$ to $C_6$ alkyl)amino, N,N-di($C_1$ to $C_6$ alkyl)amino and N,N,N-tri($C_1$ to $C_6$ alkyl)ammonio, the groups phenoxy, phenylthio, benzyloxy and benzylthio wherein in each group the phenyl ring is substituted with from 1 to 3 substituents chosen from the group consisting of halogen, nitro, cyano, $C_1$ to $C_6$ alkyl, $C_1$ to $C_6$ haloalkyl and $C_1$ to $C_6$ alkoxy, the group OM wherein M is the cation of an inorganic or organic base, the group $-NHSO_2R^3$ wherein $R^3$ is chosen from $C_1$ to $C_{10}$ alkyl and $C_1$ to $C_6$ haloalkyl, and the group $-NR^4R^5$ wherein $R^4$ and $R^5$ are independently chosen from the group consisting of hydrogen, $C_1$ to $C_6$ alkyl, phenyl and benzyl or $R^4$ and $R^5$ together form a heterocyclic ring, and the group $-O-N=R^{10}$ wherein $R^{10}$ is a $C_1$ to $C_{10}$ alkylidene group; Z is chosen from the group consisting of halogen, hydroxy, mercapto, $C_1$ to $C_{10}$ alkoxy, $C_1$ to $C_{10}$ haloalkoxy, $C_1$ to $C_{10}$ alkylthio and the group $-NR^4R^5$ wherein $R^4$ and $R^5$ are as hereinbefore defined;

X is chosen from oxygen and sulfur;

Y is chosen from oxygen, sulfur and the group $NR^6$ wherein $R^6$ is chosen from hydrogen, $C_1$ to $C_{10}$ alkyl, $C_2$ to $C_{10}$ alkenyl, $C_2$ to $C_{10}$ alkynyl, $C_2$ to $C_{10}$ alkoxyalkyl, cyanomethylene, $C_1$ to $C_6$-(alkoxy)carbonylmethylene, $C_1$ to $C_{10}$ haloalkyl, formyl, $C_2$ to $C_{10}$ alkanoyl, phenyl, benzyl, benzoyl, and the groups phenyl, benzyl and benzoyl wherein in each group the phenyl ring is substituted with from 1 to 3 substituents chosen from the group consisting of halogen, $C_1$ to $C_6$ alkyl, $C_1$ to $C_6$ haloalkyl, $C_1$ to $C_6$ alkoxy, nitro and cyano;

$\phi$ is chosen from oxygen and the group $-RAn$ wherein R is chosen from $C_1$ to $C_6$ alkyl and benzyl and An is an anion chosen from halide, tetrafluoroborate, methosulfate and fluorosulfonate;

k is chosen from 0 and 1; and n is 0, 1 or 2.

The compounds of formula I wherein $R^1$ and $R^2$ are not the same, are optically active and the present invention also includes the individual stereo isomers of such compounds, and mixtures of those stereo isomers. When W is the group

wherein G is the group OM and M is the cation of an inorganic or organic base, suitable inorganic bases include the alkali and alkaline earth metal hydroxides and carbonates, and ammonia and suitable organic bases include amines of the formula $NR^7R^8R^9$ wherein $R^7$, $R^8$ and $R^9$ are independently chosen from the group consisting of hydrogen, $C_1$ to $C_6$ alkyl, $C_1$ to $C_6$ hydroxyalkyl, phenyl and benzyl.

When W is chosen from the group

and —CH₂Z wherein G or Z is the group —NR⁴R⁵ and R⁴ and R⁵ together form a heterocyclic ring, suitable heterocyclic groups include 1-pyrrolyl, 1-imidazolyl, 1-pyrazolyl, 1-pyrrolidinyl, 1-imidazolidinyl, 1-pyrazolidinyl, 1-piperidyl, 1-piperazinyl and 4-morpholinyl.

Preferred A, B, D and E include hydrogen, halogen, C₁ to C₆ alkyl and C₁ to C₆ haloalkyl.

Preferred J¹, J², U and V include hydrogen, halogen and nitro.

Preferred R¹ and R² include hydrogen and C₁ to C₆ alkyl.

Preferred W include cyano and the group

The specific nature of G is not narrowly critical and therefore the group

may be a free carboxylic acid or a derivative thereof such as an acid salt, acid ester, acid amide, acid sulfonamide or acid oxime ester. Preferred G include hydroxy, amino, C₁ to C₁₀ alkoxy, C₂ to C₁₀ alkenyloxy, C₂ to C₁₀ alkynyloxy, cyclohexyloxy, C₁ to C₁₀ alkylthio and the group OM wherein M is an alkali metal or alkaline earth metal ion.

Preferred X is oxygen.

Preferred Y include oxygen and the group NR⁶ wherein R⁶ is chosen from hydrogen and C₁ to C₆ alkyl.

Preferred φ include oxygen and the group RAn wherein R is methyl and An is halide.

Preferred n is 0.

Among the more active compounds of the invention are those compounds of formula I in which:
A, B, D and E are chosen from hydrogen, halogen and trifluoromethyl;
J¹ and J² are independently chosen from hydrogen, halogen and nitro;
U and V are hydrogen;
R¹ is methyl;
R² is chosen from hydrogen and methyl;
W is chosen from cyano and the

wherein:
G is chosen from the group consisting of hydroxy, amino and C₁ to C₆ alkoxy;
X is oxygen;
Y is chosen from oxygen and the group NR⁶ wherein R⁶ is chosen from hydrogen and methyl;
φ is oxygen;
k is 0 or 1; and
n is 0.

Particularly preferred compounds of the invention include those compounds of formula I in which:
A, D, E, J¹, J², U, V and R² are hydrogen;
B is chosen from fluorine, chlorine, bromine, iodine and trifluoromethyl;
R¹ is methyl;
W is the group

wherein G is chosen from C₁ to C₆ alkoxy;
X and Y are oxygen; and
k and n are 0.

Examples of the compounds embraced by the invention include:
methyl 2-[4-(7-chloroquinolin-3-yloxy)phenoxy]propionate;
methyl 2-[4-(7-trifluoromethyl-1-oxide-quinolin-3-yloxy)phenoxy]propionate;
ethyl 2-[4-(7-chloroquinolin-3-yloxy)phenoxy]propionate (5);
ethyl 2-[4-(6,7-dichloroquinolin-3-yloxy)phenoxy]propionate;
ethyl 2-[4-(7,8-dichloroquinolin-3-ylthio)phenoxy]propionate;
2-[4-(7-bromoquinolin-3-yloxy)phenoxy]propiononitrile;
methyl 4-[4-(7-bromoquinolin-3-yloxy)phenoxy]valerate;
N-methanesulfonyl 2-[4-(7-chloroquinolin-3-yloxy)phenoxy]propionamide;
2-[4-(7-chloroquinolin-3-yloxy)phenoxy]propyl chloride;
methyl 2-{4-[N-(7-chloroquinolin-3-yl)-N-methylamino]phenoxy}propionate;
methyl 2-{4-[N-(2-chloroquinolin-3-yl)-N-methylamino]phenoxy}propionate;
ethyl 2{4-[N-(7-chloroquinolin-3-yl)-N-methylamino]phenoxy}propionate;
methyl 2-{4-[N-(6,7-dichloro-1-oxide-quinolin-3-yl)-N-methylamino]phenoxy}propionate;
ethyl 2-{4-[N-(7,8-dichloroquinolin-3-yl)-N-ethylamino]phenoxy}propionate;
2-{4-[N-(7-bromoquinolin-3-yl)-N-methylamino]phenoxy}propiononitrile;
methyl 4-{4-[N-(7-bromoquinolin-3-yl)amino]phenoxy}valerate;
N-methanesulfonyl 2-{4-[N-(7-chloroquinolin-3-yl)-N-methylamino]phenoxy}propionamide; and
2-{4-[N-(7-chloroquinolin-3-yl)amino]phenoxy}propyl chloride.

Particular examples of the compounds of the invention are detailed in Table 1 below.

TABLE 1

Part A

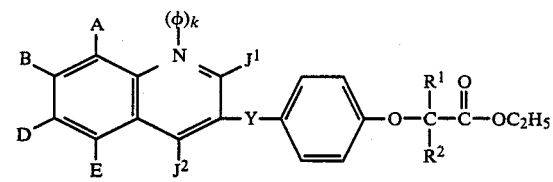

| Compound No | Substituents A, B, D, E, J¹, J² | φ | k | Y | R¹ | R² |
|---|---|---|---|---|---|---|
| 1 | all H | — | 0 | O | CH₃ | H |
| 2 | all H | O | 1 | O | CH₃ | H |
| 3 | 4-NO₂ | O | 1 | NH | CH₃ | H |
| 4 | 4-NO₂ | O | 1 | NCH₃ | CH₃ | H |
| 5 | 7-Cl | — | 0 | O | CH₃ | H |
| 6 | 7-Cl | CH₃⊕I⊖ | 1 | O | CH₃ | H |
| 7 | 6-Cl | — | 0 | O | CH₃ | H |

TABLE 1-continued

| Compound No | A, B, D E, J¹, J² | φ | k | Y | W |
|---|---|---|---|---|---|
| 8 | 6-Cl | $CH_3^\oplus I^\ominus$ | 1 | O | $CH_3$ | H |
| 9 | 6-Cl | O | 1 | O | $CH_3$ | H |
| 10 | 4-$NO_2$ | O | 1 | O | $CH_3$ | H |
| 11 | 2-Cl,4-$NO_2$ | — | 0 | $NCH_3$ | $CH_3$ | H |
| 12 | 4-$NO_2$ | — | 0 | $NCH_3$ | $CH_3$ | H |
| 13 | 6-Cl | O | 1 | O | $CH_3$ | $CH_3$ |
| 14 | 2,6-$Cl_2$ | — | 0 | O | $CH_3$ | H |
| 15 | 7-Cl | — | 0 | O | $CH_3$ | $CH_3$ |
| 16 | 2-Cl | — | 0 | O | $CH_3$ | H |
| 17 | 2-Br | — | 0 | O | $CH_3$ | H |
| 18 | 4-Cl | — | 0 | O | $CH_3$ | H |
| 19 | 4-Cl | — | 0 | $NCH_3$ | $CH_3$ | $CH_3$ |
| 20 | 7-Cl | $CH_3^\oplus I^\ominus$ | 1 | O | $CH_3$ | $CH_3$ |
| 21 | 7-Cl | — | 0 | NH | $CH_3$ | H |
| 22 | 7-$CF_3$ | — | 0 | O | $CH_3$ | H |
| 23 | 7-Cl | — | 0 | $NCH_3$ | $CH_3$ | H |
| 26 | 7-$CF_3$ | O | 1 | O | $CH_3$ | H |
| 27 | 2-Cl,7-$CF_3$ | — | 0 | O | $CH_3$ | H |
| 28 | 7-Cl | O | 1 | O | $CH_3$ | H |
| 29 | 2,7-$Cl_2$ | — | 0 | O | $CH_3$ | H |
| 30 | 7-$CF_3$ | — | 0 | NH | $CH_3$ | H |
| 31 | 7-Cl,4-$NO_2$ | O | 1 | O | $CH_3$ | H |
| 32 | 7-$CF_3$ | — | 0 | $NCH_3$ | $CH_3$ | H |
| 33 | 4,7-$Cl_2$ | — | 0 | O | $CH_3$ | H |
| 34 | 2,4,7-$Cl_3$ | — | 0 | O | $CH_3$ | H |
| 35 | 7-$CF_3$ | — | 0 | O | $CH_3$ | $CH_3$ |
| 36 | 7-$CF_3$ | O | 1 | $NCH_3$ | $CH_3$ | H |
| 40 | 7-F | — | 0 | O | $CH_3$ | H |
| 41 | 7-Cl,4-$NO_2$ | O | 1 | $NCH_3$ | $CH_3$ | H |
| 24 | 7-Cl | — | 0 | NH | $CO_2H$ |
| 25 | 7-Cl | O | 1 | $NCH_3$ | $CO_2CH_3$ |
| 37 | 7-Cl | — | 0 | O | $CO_2C_4H_9$—n |
| 38 | 7-Cl | — | 0 | O | $CO_2C_3H_7$—n |
| 39 | 7-Cl | — | 0 | O | $CONH_2$ |
| 42 | 7-F | — | 0 | O | $CO_2H$ |
| 43 | 7-F | — | 0 | O | $CO_2C_3H_7$—n |
| 44 | 7-F | — | 0 | O | $CO_2C_4H_9$—n |
| 45 | 7-Cl | — | 0 | O | CN |

Part B

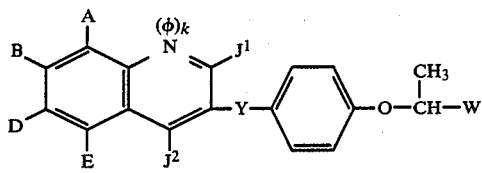

The compounds of the invention may be prepared by a variety of methods and in a further aspect the invention provides methods for the preparation of the compounds of formula I.

Compounds of formula Ia

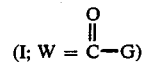

$$(I; W = \overset{O}{\underset{\|}{C}}-G)$$

wherein G is not hydroxy may be prepared from the acid of formula Ib (I; W=—$CO_2H$) by, for example, neutralisation of the acid with a base to give an acid salt, esterification of the acid with an alcohol, thiol, phenol or thiophenol to give an acid ester, or reaction of the acid (or acid halide derivative thereof) with an amine to give an amide (SCHEME A). Processes known in the art for the preparation of acid salts, acid esters, acid halides and acid amides may be adapted, without undue experimentation, to prepare compounds of the invention of formula Ia from compounds of the invention of formula Ib.

SCHEME A

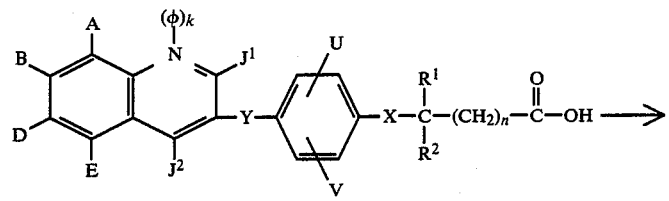

Ib

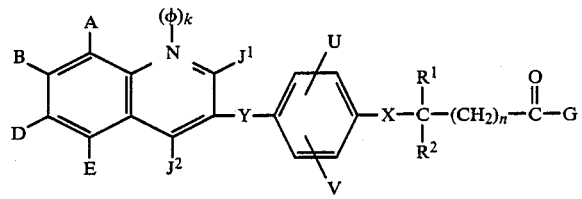

Ia

Nitriles of the invention of formula Ic (I; W=—C≡N) may be prepared, for example, from the acid amide of formula Id (I; W=—$CONH_2$) (SCHEME B).

SCHEME B

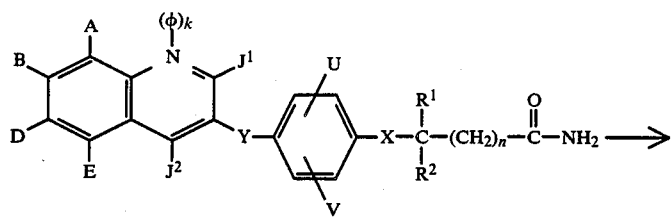

Id

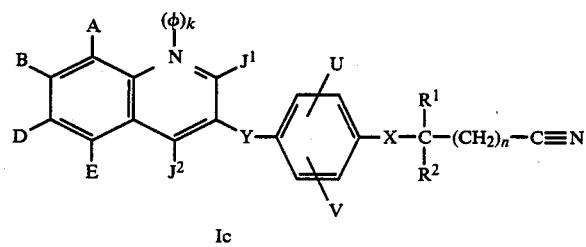

Ic

Alcohols of the invention of formula Ie (I; W=—CH$_2$OH) may be prepared from the acid or acid esters of formula If

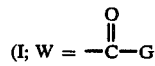

wherein G=OH or O-alkyl) by reduction (SCHEME C). Processes known in the art for the reduction of acids or acid esters to alcohols, for example lithium aluminium hydride reduction, may be adapted, without undue experimentation, to prepare alcohols of the invention of formula Ie from esters of the invention of formula If.

SCHEME C

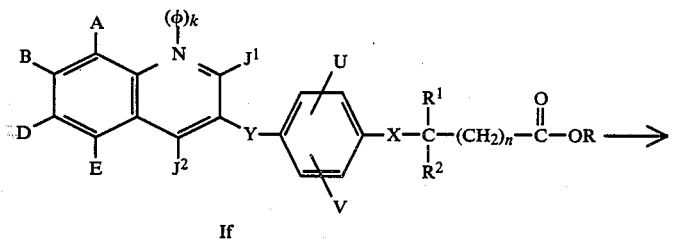

If

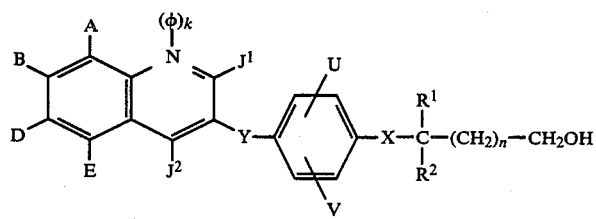

Ie

Alkyl halides of the invention of formula Ig (I; W=—CH$_2$-halogen) may be prepared from alcohols of formula Ie (I; W=—CH$_2$OH) by halogenation. Processes known in the art for the conversion of alcohols to alkyl halides, for example halogenation with reagents such as thionyl chloride, may be adapted, without undue experimentation, to prepare alkyl halides of the invention of formula Ig from alcohols of the invention of formula Ie.

Ethers of the invention of formula Ih (I; W=—CH$_2$OR) may be prepared from alcohols of formula Ie (I; W=—CH$_2$OH) by alkylation. Processes known in the art for the conversion of alcohols to ethers, for example by reaction with alkyl halides using the Williamson ether synthesis, may be adapted, without undue experimentation, to prepare ethers of the invention of formula Ih from alcohols of the invention of formula Ie.

Ethers (thioethers) of the invention of formula Ih (Ii) [I; W=—CH$_2$OR(—CH$_2$SR)] may be prepared from alkyl halides of formula Ig (I; W=CH$_2$—halogen) by alkoxylation (thiolalkyloxylation). Processes known in the art for the conversion of alkyl halides to ethers (thioethers), for example by reaction with alcohols (thiols) using the Williamson ether synthesis, may be adapted, without undue experimentation, to prepare ethers (thioethers) of the invention of formula Ih (Ii) from alkyl halides of the invention of formula Ig.

Amines of the invention of formula Ij (I; W=—CH$_2$NR$^4$R$^5$) may be prepared from the alkyl halides of formula Ig (I; W=—CH$_2$—halogen) by amination or from the amides of formula Ik

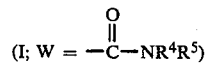

by reduction. Processes known in the art for the conversion of alkyl halides to amines, for example by reaction with amines, and for the conversion of amides to amines, for example by reduction with agents such as lithium aluminium hydride, may be adapted without undue experimentation, to prepare amines of the invention of formula Ij from alkyl halides of the invention of formula Ig and from amides of the invention of formula Ik respectively.

N-oxides of the invention of formula I wherein k is 1 may be prepared from compounds of the invention of formula I wherein K is 0 by oxidation. Processes known in the art for the conversion of quinolines to quinoline N-oxides, for example oxidations using persulfates, peroxides, peracids or peresters, may be adapted, without undue experimentation, to prepare N-oxides of the invention.

Compounds of the invention of formula I in which Y is the group $NR^6$ wherein $R^6$ is not hydrogen may be prepared from compounds of the invention of formula I in which Y is the group $NR^6$ wherein $R^6$ is hydrogen by, for example, alkylation or acylation. Processes known in the art for the preparation of derivatives of secondary amines, for example alkylation with alkyl halides and acylation with acyl halides, may be adapted, without undue experimentation, to prepare the novel compounds of the invention wherein $R^1$ is not hydrogen.

Compounds of formula I wherein A, B, D, E, U, V, $J^1$, $J^2$, 0, Y, X, $R^1$, $R^2$, W, k and n are as hereinbefore defined may be prepared by the condensation of a phenol or thiophenol of formula IX with a compound of formula X wherein hal is chlorine, bromine or iodine, preferably in the presence of an alkaline material; according to SCHEME D.

SCHEME D

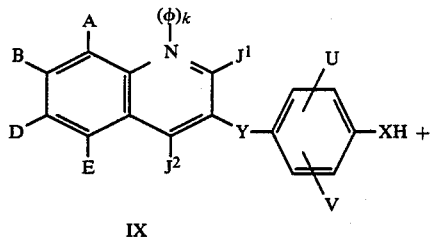

IX

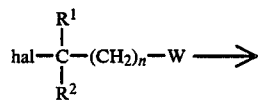

X

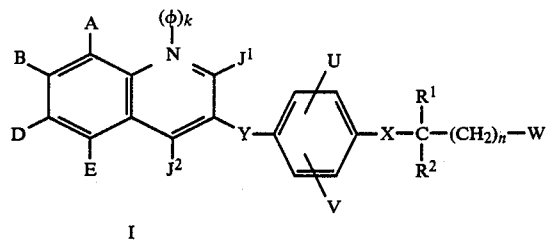

I

Compounds of formula I may also be prepared by:
(a) the condensation of the appropriate quinoline derivative of formula V, wherein L is a leaving group (for example, alkylsulfonyl, chlorine, bromine or iodine) with the appropriate compound of formula VI according to SCHEME E.

SCHEME E

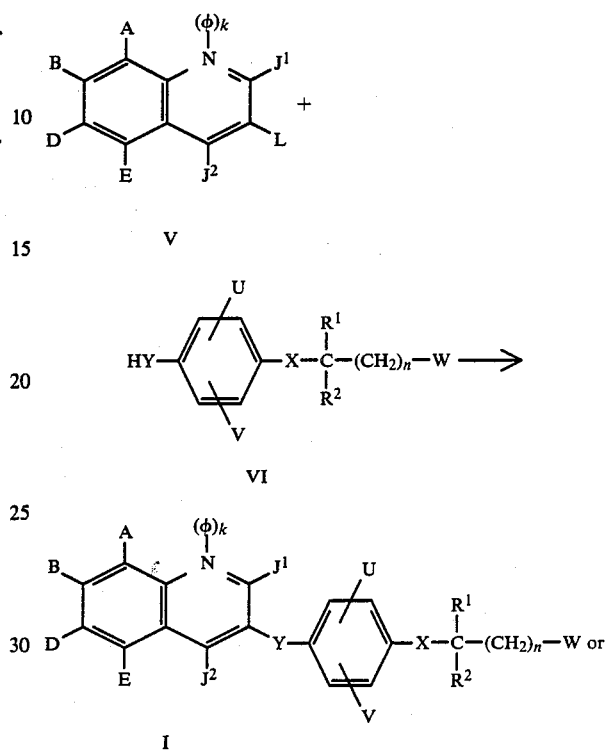

I (b) the following steps in sequence:
  (i) the condensation of the appropriate quinoline derivative of formula V, wherein L is leaving group (for example, alkylsulfonyl, chlorine, bromine or iodine) with the appropriate compound of formula VII, wherein Q is hydroxy, mercapto, $C_1$ to $C_6$ alkoxy or $C_1$ to $C_6$ alkylthio to give a compound of formula VIII wherein Q is hydroxy, mercapto, $C_1$ to $C_6$ alkoxy or $C_1$ to $C_6$ alkylthio;
  (ii) the dealkylation of the compound of formula VIII prepared in step (i) above wherein Q is $C_1$ to $C_6$ alkoxy or $C_1$ or $C_6$ alkylthio to give a compound of formula IX; and
  (iii) the condensation of the product of formula IX obtained in step (i) or step (ii) above with a compound of formula X according to the process described for SCHEME D above (Steps (i) and (ii) are shown in SCHEME F); or

SCHEME F

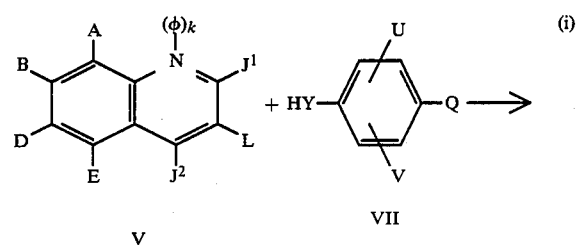

-continued

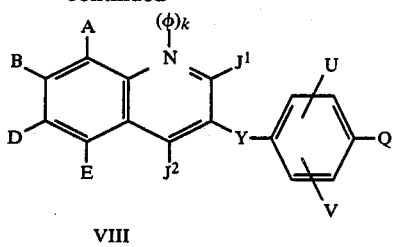

VIII

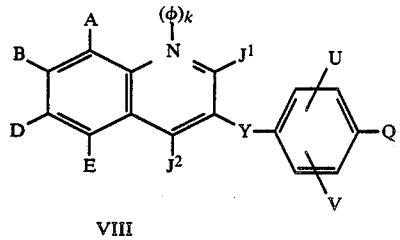

VIII

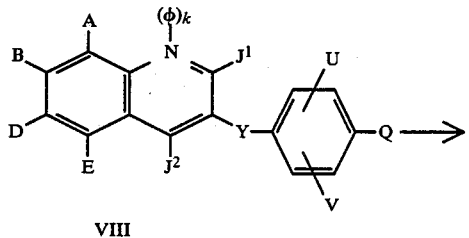

VIII

IX (c) the following steps in sequence:
 (i) the condensation of the appropriate quinoline derivative of formula XI with the appropriate benzene derivative of formula XII wherein L is a leaving group (for example, alkylsulfonyl, chlorine, bromine or iodine) and Q is hydroxy, mercapto, $C_1$ to $C_6$ alkoxy or $C_1$ to $C_6$ alkylthio, to give a compound of formula VIII wherein Q is as hereinbefore defined;
 (ii) the dealkylation of the compound of formula VIII prepared in step (i) above wherein Q is $C_1$ to $C_6$ alkoxy or $C_1$ to $C_6$ alkylthio, to give a compound of formula IX according to the process described for SCHEME F step (ii) above; and
 (iii) the condensation of the product of formula IX obtained in step (i) or step (ii) above with a compound of formula X according to the process described for SCHEME D above (step (i) is shown in SCHEME G).

SCHEME G

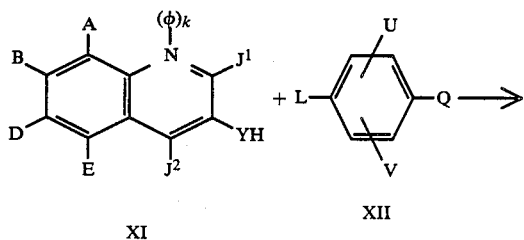

XI + XII

The condensation reaction illustrated in SCHEMES D, and E to G wherein Y is oxygen or sulfur, and outlined above, are preferably carried out in the presence of an alkaline material. Suitable alkaline materials include alkali metal and alkaline earth metal hydroxides and carbonates such as, for example, sodium hydroxide, potassium hydroxide, sodium carbonate and potassium carbonate.

The condensation reaction illustrated in Schemes D to G and outlined above are also preferably carried out in the presence of a solvent. Suitable solvents include ketones such as, for example, acetone, methyl ethyl ketone and methyl isobutyl ketone, and dipolar aprotic solvents such as, for example, dimethylformamide, dimethylacetamide, dimethylsulfoxide, N-methylpyrrolidone, hexamethylphosphoramide and sulfolan.

The reaction conditions required to effect the condensation reactions illustrated in SCHEME D, E, F, and G outlined above vary according to the nature of the reactants and the solvent used. In general the reaction is facilitated by the application of heat and usually a reaction temperature in the range of 40° to 150° C. and reaction time of between 0.5 and 20 hours is satisfactory. However, higher or lower reaction temperatures and/or shorter or longer reaction times may be used if desired.

The dealkylation reactions illustrated in SCHEMES F and G and outlined in paragraphs (b) (ii) and (c) (ii) above may be effected using a variety of reagents known in the art. For example, aryl-alkyl ethers may be cleaved using reagents such as pyridine hydrochloride, hydriodic acid, hydrobromic acid, sodium thioethoxide in dimethylformamide, acetyl p-toluenesulphonate, sodium or potassium iodide in formic or acetic acid, lithium iodide, in 2,4,6-collidine and boron tribromide. Reaction times and reaction conditions vary widely depending on the dealkylation agent used and the ether to be cleaved.

The reaction conditions generally employed when using the above "ether-cleavage" reagents are known to those skilled in the art and may be adapted without undue experimentation to effect the "ether-cleavage" reactions illustrated in SCHEMES F and G and outlined in paragraph (b) (ii) and (c) (ii) above.

The quinoline derivatives of formula V and XI which may be used to prepare the compound of the invention of formula I may be prepared by the use of one or more of the processes known in the art for the synthesis of quinoline derivatives. For example, quinoline syntheses described by:
 (i) R H F Manske & M Kulka (Skraup Reaction), Organic Reactions, Vol VII, 59 (1953)
 (ii) T J Kress & S M Constantino, J. Heterocyclic Chemistry, 10, 409 (1973).
 (iii) M Araki, et al, Chem. Pharm. Bull. (Tokyo), 16, 1742 (1968)

The compounds of formula VIII

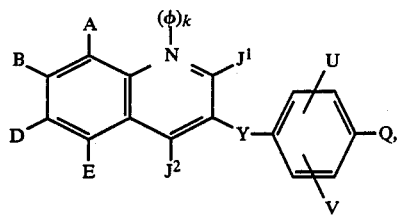

which are useful intermediate in the preparation of compounds of formula I, are novel compounds. Therefore, in a further embodiment the invention provides compounds of formula VIII wherein A, B, D, E, $J^1$, $J^2$, $\phi$, k, Y, U, V and Q are as hereinbefore defined.

The compounds of formula I are active as herbicides and therefore, in a further aspect the invention provides a process for severely damaging or killing unwanted plants which process comprises applying to the plants, or to the growth medium of the plants, an effective amount of a compound of formula I as hereinbefore defined.

Generally speaking the compounds of formula I are herbicidally effective against a variety of plants. However, certain of the compounds of the invention are selectively active against monocotyledonous plants, dicotyledonous plants being relatively unaffected by rates of application of the compounds of the invention which are severely damaging or lethal to other plant species.

Moreover, certain of the compounds of formula I are selectively active within the group of monocotyledonous plants and may be used at a rate sufficient to kill or severely damage monocotyledonous weeds in a monocotyledonous cereal corp.

Therefore, in yet a further aspect the invention provides a process for selectively controlling the growth of weeds in crops which process comprises applying to the crop, or the growth medium of the crop, a compound of formula I, as hereinbefore defined, in an amount sufficient to severly damage or kill the weeds but insufficient to damage the crop substantially.

The compounds of formula I may be applied directly to the plant (post-emergence application) or to the soil before the emergence of the plant (pre-emergence application). However, the compounds are, in general, more effective when applied to the plant post-emergence.

The compounds of formula I may be used on their own to inhibit the growth of, severely damage, or kill plants but are preferably used in the form of a composition comprising a compound of the invention in admixture with a carrier comprising a solid or liquid diluent. Therefore, in yet a further aspect the invention provides plant growth inhibiting, plant damaging, or plant killing compositions comprising a compound of formula I as hereinbefore defined and an inert carrier therefor.

Compositions according to the invention include both dilute compositions, which are ready for immediate use, and concentrated compositions, which require to be diluted before use, usually with water. Preferably the compositions contain from 0.01% to 90% by weight of the active ingredient. Dilute compositions ready for use preferably contain from 0.01% to 2% of active ingredient, while concentrated compositions may contain from 20 to 90% of active ingredient, although from 20 to 70% is usually preferred.

The solid compositions may be in the form of granules, or dusting powders wherein the active ingredient is mixed with a finely divided solid diluent, eg kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution or dispersion of an active ingredient in water optionally containing a surface-active agent, or may comprise a solution or dispersion of an active ingredient in a water-immiscible organic solvent which is dispersed as droplets in water.

Surface-cative agents may be of the cationic anionic, or non-ionic type. The cationic agents are, for for example, quaternary ammonium compounds (eg cetyltrimethylammonium bromide). Suitable anionic agents are soaps; salts of aliphatic mono esters of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate, and a mixture of the sodium salts of diisopropyl- and triisopropylnaphthalenesulphonic acid. Suitable non-ionic agents are the condensation products of ethylene oxide with fatty alcohols such as oleyl alcohol and cetyl alcohol, or with alkylphenols such as octyl- or nonyl-phenol or octyl-cresol. Other non-ionic agents are the partial esters derived from long chain fatty acids and hexitol anhydrides, for example sorbitan monolaurate; the condensation products of the partial ester with ethylene oxide; and the lecithins.

The aqueous solutions or dispersions may be prepared by dissolving the active ingredient in water or an organic solvent optionally containing wetting or dispersing agent(s) and then, when organic solvents are used, adding the mixture so obtained to water optionally containing wetting or dispersing agent(s). Suitable organic solvents include, for example, ethylene dichloride, isopropyl alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a high proportion of the active ingredient, and the concentrate is then diluted with water before use. The concentrates are usually required to withstand storage for prolonged periods and after such storage, to be capable of dilution with water to form aqueous preparations which remain homogeneous for a sufficient time to enable them to be applied by conventional spray equipment. Concentrates conveniently contain 20–90%, preferably 20–70%, by weight of the active ingredient(s). Dilute preparations ready for use may contain varying amounts of the active ingredient(s) depending upon the intended purpose; amounts of 0.01% to 10.0% and preferably 0.1% to 2%, by weight of active ingredient(s) are normally used.

A preferred form of concentrated composition comprising the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragacanth. Preferred suspending agents are those which impart thixotropic properties to, and increase the viscosity of the concentrate. Examples of preferred suspending agents include hydrated colloidal mineral silicates, such as montmorillonite, beidellite, nontronite, hectorite, saponite, and sauconite. Bentonite is especially preferred. Other suspending agents include cellulose derivatives and polyvinyl alcohol.

The rate of application of the compounds of the invention will depend on a number of factors including, for example, the compound chosen for use, the identity of the plants whose growth is to be inhibited the formulations selected for use and whether the compound is to be applied for foliage or root uptake. As a general guide, however, an application rate of from 0.005 to 20 kilograms per hectare is suitable while from 0.05 to 5.0 kilograms per hectare may be preferred.

The compositions of the invention may comprise, in addition to one or more compounds of the invention, one or more compounds not of the invention but which possess biological activity. For example, as hereinbefore indicated the compounds of the invention are in general substantially more effective against monocotyledonous plants or grass species than against dicotyledonous plants or broad-leaved species. As a result, in certain applications the herbicidal use of the compounds of the invention alone may be sufficient to protect a crop. Accordingly in yet still further embodiment the invention provides a herbicidal composition comprising a mixture of at least one herbicidal compound of formula I as hereinbefore defined with at least one other herbicide.

The other herbicide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

Examples of useful complementary herbicides include:

A. benzo-2,1,3-thiadiazin-4-one-2,2-dioxides such as 3-isopropylbenzo-2,1,3-thiadiazin-4-one-2,2-dioxide (common name bentazon);

B. hormone herbicides and in particular the phenoxyalkanoic acids such as 4-chloro-2-methylphenoxy acetic acid (common name MCPA), 2-(2,4-dichlorophenoxy) propionic acid (common name dichlorprop), 2,4,5-trichlorophenoxyacetic acid (common name 2,4,5-T), 4-(4-chloro-2-methylphenoxy)butyric acid (common name MCPB), 2,4-dichlorophenoxyacetic acid (common name 2,4-D), 4-(2,4-dichlorophenoxy)butyric acid (common name 2,4-DB), 2-(4-chloro-2-methylphenoxy)propionic acid (common name mecoprop), and their derivatives (eg salts, esters, amides and the like);

C. 3-[4-(4-halophenoxy)phenyl]-1,1-dialkylureas such as 3-[4-(4-chlorophenoxy)phenyl]-1,1-dimethylurea (common name chloroxuron);

D. dinitrophenols and their derivatives (eg acetates) such as 2-methyl-4,6-dinitrophenol (common name DNOC), 2-tertiarybutyl-4,6-dinitrophenol (common name dinoterb), 2-secondarybutyl-4,6dinitrophenol (common name dinoseb) and its ester dinoseb acetate;

E. dinitroaniline herbicides such as N', N'-diethyl-2,6dinitro- 4-trifluoromethyl-m-phenylenediamine (common name dinitramine), 2,6-dinitro-N,N-dipropyl-4-trifluoromethylaniline (common name trifluralin) (common name nitralin);

F. phenylurea herbicides such as N'-(3,4-dichlorophenyl)-N,N-dimethylurea (common name diuron) and N,N-dimethyl-N'-[3-(trifluoromethyl)phenyl]urea (common name fluometuron);

G. phenylcarbamoyloxyphenylcarbamates such as 3-[(methoxycarbonyl)amino]phenyl (3-methylphenyl)-carbamate (common name phenmedipham) and 3-[(ethoxycarbonyl)amino]phenyl phenylcarbamate (common name desmedipham);

H. 2-phenylpyridazin-3-ones such as 5-amino-4-chloro-2-phenylpyridazin-3-one (common name pyrazon);

I. uracil herbicides such as 3-cyclohexyl-5,6-trimethyleneuracil (common name lenacil), 5-bromo-3-sec-butyl-6-methyluracil (common name bromacil) and 3-tert-butyl-5-chloro-6-methyluracil (common name terbacil);

J. triazine herbicides such as 2-chloro-4-ethylamino-6-(iso-propylamino)-1,3,5-triazine (common name atrazine), 2-chloro-4,6-di(ethylamino)-1,3,5-triazine (common name simazine) and 2-azido-4-(iso-propylamino)-6-methylthio-1,3,5-triazine (common name azipropytryne);

K. 1-alkoxy-2-alkyl-3-phenylurea herbicides such as 3-(3,4-dichlorophenyl)-1-methoxy-1-methylurea (common name linuron), 3-(4-chlorophenyl)-1-methoxy-1-methylurea (common name monolinuron) and 3-(4-bromo-4-chlorophenyl)-1-methoxy-1-methylurea (common name chlorobromuron);

L. thiolcarbamate herbicides such as S-propyl dipropyl-thiocarbamate (common name verolate);

M. 1,2,4-triazin-5-one herbicides such as 4-amino-4,5-dihydro-3-methyl-6-phenyl-1,2,4-triazine-5-one (common name metamitron) and 4-amino-6-tert-butyl-4,5-dihydro-3-methylthio-1,3,4-triazin-5-one (common name metribuzin);

N. benzoic acid herbicides such as 2,3,6-trichlorobenzoic acid (common name 2,3,6-TBA), 3,6-dichloro-2-methoxybenzoic acid (common name dicamba) and 3-amino-2,5-dichlorobenzoic acid (common name chloramben).

O. anilide herbicides such as N-butoxymethyl-α-chloro-2',6'-diethylacetanilide (common name butachlor), the corresponding N-methoxy compound (common name alachlor), the corresponding N-iso-propyl compound (common name propachlor) and 3',4'-dichloropropionanilide (common name propanil);

P. dihalobenzonitrile herbicides such as 2,6-dichlorobenzonitrile (common name dichlobenil), 3,5-dibromo-4-hydroxybenzonitrile (common name bromoxynil) and 3,5-diiodo-4-hydroxybenzonitrile (common name ioxynil).

Q. haloalkanoic herbicides such as 2,2-dichloropropionic acid (common name dalapon), trichloroacetic acid (common name TCA) and salts thereof;

R. diphenylether herbicides such as 4-nitrophenyl 2-nitro-4-trifluoromethylphenyl ether (common name fluorodifen), methyl 5-(2,4-dichlorophenoxy)-2-nitrobenzoate (common name bifenox), 2-nitro-5-(2-chloro-4-trifluoromethylphenoxy)benzoic acid and 2-chloro-4-trifluoromethylphenyl 3-ethoxy-4-nitrophenyl ether; and S. miscellaneous herbicides including N,N-dimethyldiphenylacetamide (common name diphenamid), N-(1-naphthyl)phthalamic acid (common name naptalam) and 3-amino-1,2,4-triazole.

Examples of useful contact herbicides include:

T. bipyridylium herbicides such as those in which the active entity is the 1,1'-dimethyl-4,4'-dipyridylium ion (common name paraquat) and those in which the active entity is the 1,1'-ethylene-2,2'-dipyridylium ion (common name diquat);

U. organoarsenical herbicides such as monosodium methanearsonate (common name MSMA); and V. amino acid herbicides such as N-(phosphonomethyl)glycine (common name glyphosate) and its salts and esters.

The invention is now illustated by, but in no way limited to, the following Examples.

EXAMPLE 1

Ethyl 2-[4-(quinolin-3-yloxy)phenoxy]propionate (1)

(a) 4-Methoxyphenol (7 g) was stirred with potassium hydroxide (2.6 g) at 150° C. for 3 hours. Water formed during the reaction was removed under reduced pressure. 3-Bromoquinoline (5 g) and copper powder (0.1 g) were then added and the mixture was stirred and heated at 200° C. for 2 hours. After cooling the mixture was partitioned between diethyl ether and water. The ether layer was separated and dried and the solvent was removed under reduced pressure to give 3-(4-methoxyphenoxy)quinoline as a dark solid which was recrystallized from petroleum ether to give pale yellow crystals (2.6 g), mp 104° C.

(b) A mixture of 3-(4-methoxyphenoxy)quinoline (2.6 g), acetic acid (20 ml) and hydrobromic acid (20 ml of 48%) was boiled under reflux for 5 hours. The solution was concentrated under reduced pressure, poured onto ice and the resultant precipitate was collected by filtration to give 3-(4-hydroxyphenoxy)-quinoline as a dark brown solid (2.4 g), mp 250° C.

(c) A mixture of 3-(4-hydroxyphenoxy)quinoline (2.4 g), ethyl 2-bromopropionate (2.1 g), anhydrous potassium carbonate (3.3 g) and dimethylformamide (50 ml) was stirred and heated at 80° C. for 4 hours. The mixture was poured into water (500 ml) and extracted with diethyl ether (2×100 ml). The ether extracts were dried, evaporated to dryness and then chromatographed on silica gel (100 g) with dichloromethane elution. Ethyl 2-[4-(3-quinolinyloxy)phenoxy]propionate was obtained as a pale yellow oil (1.9 g). Proton magnetic resonance spectrum (CDCl$_3$; $\delta$ in ppm): 8.75 (1H, d); 8.1 (1H, bd); 7.7–7.3 (4H, m); 7.0 (4H, s, phenoxy protons); 4.75 (1H, q, C$\underline{H}$-CH$_3$); 4.25 (2H, q, OC$\underline{H}_2$-CH$_3$); 1.65 (3H, d, CH-C$\underline{H}_3$); 1.25 (3H, t, OCH$_2$-C$\underline{H}_3$).

EXAMPLE 2

Ethyl 2-[4-(1-oxide-quinolin-3-yloxy)phenoxy]propionate (2)

A solution of ethyl 2-[4-(3-quinolinyloxy)phenoxy]-propionate (1.1 g) and 3-chloroperoxybenzoic acid (0.65 g) in dichloromethane (50 ml) was kept at 20° C. for 4 days. The solution was washed with aqueous 5% sodium metabisulphite solution and then with aqueous 5% sodium bicarbonate and then it was dried and evaporated to give an orange oil. Chromatography over silica gel (40 g) with dichloromethane elution gave ethyl 2-[4-(1-oxide-3-quinolinyloxy)phenoxy]propionate (1.19 g) as a pale brown viscous oil. Mass spectrum (m/e): 353 (parent ion; 100%); 337 (40%); 280 (60%); 236 (55%).

EXAMPLE 3

Ethyl 2-{4-[N-(4-nitro-1-oxidequinolin-3-yl)amino]phenoxy}propionate (3)

(a) A solution of 4-aminophenol (390 mg) in 50% aqueous acetonitrile (10 ml) was added slowly to a stirred suspension of 3-fluoro-4-nitroquinoline-1-oxide (400 mg; prepared according to the method described by M. Araki et al, *Chem. Pharm. Bull.* (*Tokyo*), 16(9), 1742–6, 1968) in acetonitrile (20 ml). After the reaction mixture had been stirred at room temperature for a period of 15 minutes thin layer chromatography indicated that the reaction was complete. The red precipitate was collected by filtration, washed with water and dried to give 4-[N-(4-nitro-1-oxidequinolin-3-yl)amino]phenol (500 mg; 91%).

(b) A mixture of 4-[N-(4-nitro-1-oxidequinolin-3-yl)amino]phenol (500 mg), ethyl 2-bromopropionate (0.33 g), anhydrous potassium carbonate (0.35 g), potassium iodide (0.05 g) and methyl ethyl ketone (10 ml) was heated under reflux for a period of 3 hours. After cooling the reaction mixture was poured into water (150 ml) and the aqueous solution was extracted with ethyl acetate. The organic phase was separated, washed with water and dried over anhydrous magnesium sulfate. The solvent was removed by distillation under reduced pressure to give a yellow solid. The solid was recrystallised from methanol to give ethyl 2-{4-[N-(4-nitro-1-oxidequinolin-3-yl)amino]phenoxy}propionate (530 mg; 79%) as yellow needles, mp 114° C.

EXAMPLE 4

Ethyl 2-{4-[N-methyl-N-(4-nitro-1-oxidequinolin-3-yl)amino]phenoxy}propionate (4)

(a) 3-Fluoro-4-nitroquinoline-1-oxide (500 mg; see Example 3 part (a)) was added to a solution of 4-(N-methylamino)phenol sulfate salt (788 mg) and sodium hydrogen carbonate in a mixture of water (10 ml) and acetonitrile (30 ml) and the mixture was heated and stirred at a temperature of 60° C. for a period of 30 minutes. The precipitate was collected by filtration, washed with water and dried to give 4-[N-methyl-N-(4-nitro-1-oxidequinolin-3-yl)amino]phenol (515 mg).

(b) 4-[N-Methyl-N-(4-nitro-1-oxidequinolin-3-yl)amino]phenol and ethyl 2-bromopropionate were reacted following essentially the same procedure as that described in Example 3 part (b) to give ethyl 2-{4-[N-methyl-N-(4-nitro-1-oxidequinolin-3-yl)amino]phenoxy}propionate as a dark red solid, mp 98° C.

EXAMPLE 5

Ethyl 2-{4-[(7-chloroquinolin-3-yl)oxy]phenoxy}propionate (5) was prepared from 3-bromo-7-chloroquinoline, 4-methoxyphenol and ethyl 2-bromopropionate following essentially the same procedure as that described in Example 1 parts (a), (b) and (c). The product, a pale yellow oil, was characterized by its proton magnetic resonance spectrum. Pmr spectrum (CDCl$_3$; $\delta$ in ppm): 9.75 (1H, d); 8.06 (1H, bs); 7.41 (3H, m); 7.00 (4H, s); 4.75 (1H, q); 4.21 (2H, q); 1.62 (3H, d); 1.27 (3H, t).

EXAMPLE 6

Ethyl 2-{4-[(7-chloro-1-methylquinolinium-3-yl)oxy]phenoxy}propionate iodide salt (6) was prepared by reacting a mixture of ethyl 2-{4-[(7-chloroquinolin-3-yl)oxy]phenoxy}propionate (see Example 5) and methyl iodide in dichloromethane at ambient temperature for a period of four days. The product, a viscous oil, was characterized by its proton magnetic resonance spectrum. Pmr spectrum (CDCl$_3$; $\delta$ in ppm): 9.8 (1H, d); 8.6 (2H, m); 8.3 (1H, d); 7.75 (1H, d of d); 7.1 (4H, d of d); 4.8 (4H, m); 4.15 (2H, q); 1.55 (3H, d); 1.25 (3H, t).

EXAMPLE 7

Ethyl 2-{4-[(6-chloroquinolin-3-yl)oxy]phenoxy}propionate (7) was prepared from 3-bromo-6-chloroquinoline, 4-methoxyphenol and ethyl 2-bromopropionate following essentially the same procedure as that described in Example 1 parts (a), (b) and (c). The product recrystallised from methanol as colourless crystals, mp 98° C.

EXAMPLE 8

Ethyl 2-{4-[(6-chloro-1-methylquinolin-3-yl)oxy]phenoxy}propionate iodide salt (8) was prepared by reacting a mixture of ethyl 2-{4-[(6-chloroquinolin-3-yl)oxy]phenoxy}propionate (see Example 7) and methyl iodide in dichloromethane at ambient temperature for a period of four days. The product, a viscous oil, was characterized by its proton magnetic resonance spectrum. Pmr spectrum (CDCl$_3$; in ppm): 10.1 (1H, d); 8.8 (1H, d); 8.65 (1H, d); 8.5 (1H, d); 8.05 (1H, d of d); 7.3 (4H, d of d); 4.95 (4H, m); 4.25 (2H, q); 1.6 (3H, d); 1.2 (3H, t).

EXAMPLE 9

Ethyl 2-{4-[(6-chloro-1-oxidequinolin-3-yl)oxy]phenoxy}propionate (9) was prepared from ethyl 2-{4-[(6-chloroquinolin-3-yl)oxy]phenoxy}propionate (see Example 7) following essentially the same procedure as that described in Example 2. The product was a pale tan crystalline solid, mp 144° C.

EXAMPLE 10

Ethyl 2-{4-[(4-nitro-1-oxidequinolin-3-yl)oxy]phenoxy}propionate (10)

A mixture of 3-fluoro-4-nitroquinoline-1-oxide (1.0 g), ethyl 2-(4-hydroxyphenoxy)propionate (1.0 g), anhydrous potassium carbonate (0.8 g) and methyl ethyl ketone (10 ml) was heated and stirred at a temperature of 80° C. for a period of 2 hours. The mixture was cooled and poured into water (150 ml) and the aqueous mixture was extracted with ethyl acetate (2×50 ml). The combined organic phases were washed with water, dried over anhydrous magnesium sulfate and the solvent was removed by distillation under reduced pressure. The solid residue was chromatographed over silica gel (eluent dichloromethane/ethyl acetate 7:1) to give ethyl 2-{4-[(4-nitro-1-oxidequinolin-3-yl)oxy]phenoxy}propionate (1.5 g) as a yellow solid. The product was characterised by proton magnetic resonance spectroscopy. Pmr spectrum (CDCl$_3$; $\delta$ in ppm); 8.3 (1H, m); 7.9 (1H, s); 7.5 (3H, m); 6.9 (4H, d of d); 4.65 (1H, q); 4.15 (2H, q); 1.6 (3H, d); 1.2 (3H, t).

EXAMPLE 11

Ethyl 2-{4-[N-(2-chloro-4-nitroquinolin-3-yl)-N-methylamino]phenoxy}propionate (11) and ethyl 2-{4-[N-methyl-N-(4-nitroquinolin-3-yl)amino]phenoxy}propionate (12)

A solution of ethyl 2-{4-[N-methyl-N-(4-nitro-1-oxidequinolin-3-yl)amino]phenoxy}propionate (6.0 g; see Example 4) in dry ethanol-free chloroform (50 ml) was cooled to a temperature of 0° C. under an atmosphere of dry nitrogen. Phosphorus trichloride (4.0 g) was added dropwise to the stirred solution the temperature of the reaction mixture being maintained between 0° and 8° C. throughout the addition. On completion of the addition the reaction mixture was stirred at a temperature of 0° to 8° C. for a further period of 40 minutes and then was poured into ice-water. The aqueous mixture was made basic by the addition of saturated aqueous sodium bicarbonate solution and then extracted with dichloromethane (2×100 ml). The combined organic extracts were dried over anhydrous magnesium sulfate and the solvent was removed by distillation under reduced pressure. The product, a dark red oil, was chromatographed over silica gel (eluent dichloromethane followed by dichloromethane/ethyl acetate 7:1) to give, as the major product, ethyl 2-{4-[N-methyl-N-(4-nitroquinolin-3-yl)amino]phenoxy}propionate as an oil. The product was characterised by proton magnetic resonance spectroscopy. Pmr spectrum (CDCl$_3$; $\delta$ in ppm); 8.6 (1H, s); 7.85 (1H, m); 7.4 (3H, m); 6.7 (4H, s); 4.6 (1H, q); 4.1 (2H, q); 3.25 (3H, s); 1.55 (3H, d); 1.2 (3H, t).

Chromatography also gave as a minor product ethyl 2-{4-[N-(2-chloro-4-nitroquinolin-3-yl)-N-methylamino]phenoxy}propionate as an oil. The product was characterised by proton magnetic resonance spectroscopy. Pmr spectrum (CDCl$_3$; $\delta$ in ppm); 8.4 (1H, m); 8.0 (3H, m); 7.05 (4H, d of d); 4.85 (1H, q); 4.35 (2H, q); 3.3 (3H, s); 1.5 (3H, d); 1.2 (3H, t).

EXAMPLE 12

Ethyl 2-{4-[(6-chloroquinolin-3-yl)oxy]phenoxy}-2-methylpropionate (13) was prepared from 4-[(6-chloroquinolin-3-yl)oxy]phenol and ethyl 2-bromo-2-methylpropionate following essentially the same procedure as that described in Example 1 part (c). The product, a pale yellow oil, was characterised by mass spectrometry. Mass spectrum (m/e, %): 387 (M+, 13); 385 (M+, 35), 271 (100).

EXAMPLE 13

Ethyl 2-{4-[(2,6-dichloroquinolin-3-yl)oxy]phenoxy}propionate (14)

(a) A mixture of hydrogen peroxide (15 ml of 40% aqueous) and acetic acid (17 ml) was added to a solution of 4-[(6-chloroquinolin-3-yl)oxy]phenol (14.0 g) in acetic acid (68 ml) and the mixture was heated and stirred at a temperature of 100° C. for a period of 10 hours. The reaction mixture was concentrated and and the precipitated solid was collected by filtration and dried. The brown solid was added portionwise to phosphoryl chloride (50 ml) and the resulting mixture was heated at a temperature of 80° C. for a period of 15 minutes. The reaction mixture was cooled and poured into ice. The resulting aqueous suspension was extracted with ethyl acetate (2×100 ml), the combined organic phases were dried over anhydrous magnesium sulfate, and the solvent was removed by distillation under reduced pressure to give 4-[(2,6-dichloroquinolin-3-yl)oxy]phenol as a tan solid.

(b) Ethyl 2-{4-[(2,6-dichloroquinolin-3-yl)oxy]phenoxy}propionate was prepared by reacting 4-[(2,6-dichloroquinolin-3-yl)oxy]phenol and ethyl 2-bromopropionate following essentially the same procedure as that described in Example 1 part (c). The product was obtained as a solid, mp 56° C.

EXAMPLE 14

Ethyl 2-{4-[(7-chloroquinolin-3-yl)oxy]phenoxy}-2-methylpropionate (15) was prepared from 4-[(7-chloroquinolin-3-yl)oxy]phenol and ethyl 2-bromo-2-methylpropionate following essentially the same procedure as that described in Example 1 part (c). The product, a pale yellow oil was characterised by proton magnetic resonance spectroscopy. Pmr spectrum (CDCl$_3$; δ in ppm): 8.65 (1H, d); 7.95 (1H, bs); 7.35 (3H, m); 6.9 (4H, s); 4.2 (2H, q); 1.6 (6H, s); 1.2 (3H, t).

EXAMPLE 15

Ethyl 2-{4-[(2-chloroquinolin-3-yl)oxy]phenoxy}propionate (16)

A mixture of ethyl 2-{4-[(1-oxidequinolin-3-yl)oxy]phenoxy}propionate (2.0 g; see Example 2) and phosphorus oxychloride (10 ml) was heated to a temperature of 80° C. for a period of 15 minutes. The reaction mixture was cooled and poured onto ice and the aqueous mixture was extracted with dichloromethane (2×100 ml). The combined organic phases were washed with aqueous sodium bicarbonate solution and dried over anhydrous magnesium sulfate. The solvent was removed by distillation under reduced pressure and the residue was chromatographed over silica gel (eluent dichloromethane followed by a mixture of dichloromethane/ethyl acetate 7:1) to give ethyl 2-{4-[(2-chloroquinolin-3-yl)oxy]phenoxy}propionate as an oil. The product was characterised by proton magnetic resonance spectroscopy. Pmr spectrum (CDCl$_3$ δ in ppm): 7.5–8.05 (4H, m); 7.4 (1H, s); 7.0 (4H, s); 4.75 (1H, q); 4.2 (2H, q); 1.75 (3H, d); 1.3 (3H, t).

EXAMPLE 16

Ethyl 2-{4-[(2-bromoquinolin-3-yl)oxy]phenoxy}propionate (17) was prepared by reacting ethyl 2-{4-[(1-oxidequinolin-3-yl)oxy]phenoxy}propionate and phosphorus oxybromide following essentially the same procedure as that described in Example 15. The product was characterised by mass spectrometry. Mass spectrum (m/e; %): 415 (M+) 314 (37); 206 (22); 101 (26); 29 (100).

EXAMPLE 17

Ethyl 2-{4-[(4-chloroquinolin-3-yl)oxy]phenoxy}propionate (18) was prepared by reacting ethyl 2-{4-[(4-nitro-1-oxidequinolin-3-yl)oxy]phenoxy}propionate (see Example 10) and phosphorus trichloride following essentially the same procedure as that described in Example 11. The product was characterised by proton magnetic resonance spectroscopy. Pmr spectrum (CDCl$_3$, δ in ppm): 8.6 (1H, s); 7.9–8.2 (2H, m); 7.5–7.8 (2H, m); 6.95 (4H, d of d); 4.7 (1H, q); 4.15 (2H, q); 1.65 (3H, d); 1.25 (3H, t).

EXAMPLE 18

Ethyl 2-{4-[N-(4-chloroquinolin-3-yl)-N-methylamino]phenoxy}-2-methylpropionate (19)

(a) Ethyl 2-{4-[N-methyl-N-(4-nitro-1-oxidequinolin-3-yl)amino]phenoxy}-2-methylpropionate was prepared from 4-[N-methyl-N-(4-nitro-1-oxidequinolin-3-yl)amino]phenol and ethyl 2-bromo-2-methylpropionate following essentially the same procedure as that described in Example 1 part (c).

(b) A solution of phosphorus trichloride (0.8 g) in dry, ethanol-free chloroform (1 ml) was added dropwise to a solution of ethyl 2-{4-[N-methyl-N-(4-nitro-1-oxidequinolin-3-yl)amino]phenoxy}-2-methylpropionate (1.0 g) in dry, ethanol-free chloroform (20 ml) stirred under a nitrogen atmosphere. The mixture was heated under reflux for a period of 5 minutes, cooled and poured onto ice. The aqueous mixture was extracted with ethyl acetate (2×100 ml) and the combined organic phases were dried over anhydrous magnesium sulfate. The solvents were removed by distillation under reduced pressure and the residue was chromatographed over silica gel (eluent dichloromethane) to give ethyl 2-{4-[N-(4-chloroquinolin-3-yl)-N-methylamino]phenoxy}-2-methylpropionate as an oil. The product was characterised by proton magnetic resonance spectroscopy. Pmr spectrum (CDCl$_3$, δ in ppm): 8.7 (1H, s); 8.0–8.4 (2H, m); 7.5–7.8 (2H, m); 6.7 (4H, d of d); 4.2 (2H, q); 3.4 (3H, s); 1.45 (6H, s); 1.30 (3H, t).

EXAMPLE 19

Ethyl 2-{4-[N-(7-chloroquinolin-3-yl)amino]phenoxy}propionate (21)

(a) A mixture of 3-bromo-7-chloroquinoline (15 g, 0.062 mole), 4-methoxyacetanilide (9.75 g, 0.059 mole) anhydrous potassium carbonate (8.8 g, 0.064 mole) and copper powder (200 mg) was heated with stirring at 200° C. for 5 hours under an atmosphere of nitrogen. The mixture was allowed to cool, ethyl acetate was added and the resultant mixture was filtered through celite. The filtrate was then washed with water, dried over magnesium sulphate and evaporated to give a brown oil (22.6 g). Purification by chromatography over silica gel using methylene chloride/ethyl acetate as solvent gave 3-[N-acetyl-N-(4-methoxyphenyl)amino]-7-chloroquinoline as a brown oil (13.6 g, 70%) which was characterized by its proton magnetic resonance spectrum (CDCl$_3$; δ in ppm): 8.9 (1H, bs); 8.15 (1H, bs); 7.9 (1H, bs); 7.4–7.8 (2H, m); 7.1 (4H, d of d); 3.8 (3H, s); 2.1 (3H, s).

(b) A mixture of 3-[N-acetyl-N-(4-methoxyphenyl)amino]-7-chloroquinoline (13.0 g), acetic acid (90 ml) and hydrobromic acid (48%, 90 ml) was heated under reflux with stirring for 5 hours. The solvent was evaporated under reduced pressure and the residue was partitioned between ethyl acetate and dilute aqueous sodium bicarbonate. The organic layer was separated, dried over magnesium sulphate and evaporated to give 4-[N-(7-chloroquinolin-3-yl)amino]phenol as a dark yellow solid (9 g, 85%, mp 218° C.

(c) 4-N-(7-Chloroquinolin-3-yl)amino]phenol and ethyl 2-bromopropionate were reacted following essentially the same procedure as that described in Example 3 part (b) to give ethyl 2-{4-[N-(7-chloroquinolin- 3-yl)amino]phenoxy}propionate as an oil which was characterised by its proton magnetic resonance spectrum (Table 3).

EXAMPLE 20

Ethyl 2-{4-[N-methyl-N-(7-chloroquinolin-3-yl)amino]-phenoxy}propionate (23)

To a solution of ethyl 2-{4-[N-(7-chloroquinolin-3-yl)amino]phenoxy}propionate (2.6 g, 6.8 mmoles) in dimethylformamide (15 ml) was added at 20° C. with stirring sodium hydride (0.35 g, 14 mmoles). After 0.5 hours methyl iodide (3 g, 21 mmoles) was added and stirring was continued for a further 1.5 hours at 30° C. The solution was poured into water (200 ml) and extracted with ethyl acetate (100 ml). The organic layer was washed with water, dried over magnesium sulphate and evaporated to give the crude product which was purified by chromatography over silica gel. Ethyl 2-{4[N-methyl-N-(7-chloroquinolin-3-yl)amino]phenoxy}propionate was isolated as pale yellow oil and characterised by its proton magnetic resonance spectrum (Table 3).

EXAMPLE 21

2-{4-[N-(7-Chloroquinolin-3-yl)amino]phenoxy}propionic acid (24)

A solution of ethyl 2-{4-[N-(7-chloroquinolin-3-yl)amino]phenoxy}propionate (370 mg) and potassium hydroxide (200 mg) in methanol (10 ml) was warmed and stirred for 24 hours. The solution was poured into dilute hydrochloric acid (50 ml of 0.5M) and extracted with ethyl acetate (2×50 ml). The organic layer was dried over magnesium sulphate, filtered and evaporated to give 2-{4-[N-(7-chloroquinolin-3-yl)amino]phenoxy}propionic acid (200 mg) as a brown solid, mp 150° C.

EXAMPLE 22 n-Propyl 2-[4-(7-chloroquinolin-3-yloxy)phenoxy]propionate (37)

A mixture of ethyl 2-[4-(7-chloroquinolin-3-yloxy)-phenoxy]propionate (500 mg), concentrated sulphuric acid (2 drops) and n-propanol (50 ml) was heated under reflux with stirring for 72 hours. The solvent was removed under reduced pressure and the residue was partitioned between dichloromethane and water. The organic layer was separated, dried over magnesium sulphate and evaporated to give n-propyl 2-[4-(7-chloroquinolin-3-yloxy)phenoxy]propionate as a pale brown oil which was characterised by its proton magnetic resonance spectrum (Table 3).

EXAMPLE 23

2-[4-(7-chloroquinolin-3-yloxy)phenoxy]propionamide (39)

Concentrated ammonia was added at 20° C. to a solution of ethyl 2-[4-(7-chloroquinolin-3-yloxy)phenoxy]-propionate (3.0 g) (see Example 5) in acetone (50 ml) until the mixture just began to turn cloudy. The mixture was then heated at 60° C. for 8 hours and allowed to cool and stand overnight. Colourless crystals (1.5 g) 2-[4-(7-chloroquinolin-3-yloxy)phenoxy]propionamide were collected by filtration. The compound was characterised by its proton magnetic resonance spectrum. (Table 3).

EXAMPLE 24

2-[4-(7-Chloroquinolin-3-yloxy)phenoxy]propionitrile (45)

2-[4-(7-Chloroquinolin-3-yloxy)phenoxy]propionamide (see Example 23) (1.2 g) was added slowly with stirring to phosphorus oxychloride (10 ml) at 20° C. The mixture was heated briefly to the boiling point then poured on to water and neutralized carefully with aqueous sodium bicarbonate solution. Extraction with ethyl acetate gave, after drying and evaporation, the crude product as a pale yellow oil. Purification by chromatography on silica gel gave 2-[4-(7-chloroquinolin-3-yloxy)phenoxy]propionitrile, characterised by its proton magnetic resonance spectrum (Table 3).

EXAMPLE 25

The compounds of the invention listed in Table 2 below (see Table 1 four compound no code) were prepared by the method indicated.

TABLE 2

| Compound No | Prepared by Method of Example No | Melting Point °C. |
| --- | --- | --- |
| 20 | 6 | 150 |
| 26 | 2 | 109 |
| 42 | 21 | 80 |

EXAMPLE 26

The compounds of the invention listed in Table 3 below (see Table 1 for compound no code) were prepared by the method indicated.

TABLE 3

| Compound No | Method of Example | Proton Magnetic Resonance Spectrum Chemical Shift δ in ppm |
| --- | --- | --- |
| 21 | 19 | 8.7 (1H,d); 7.95 (1H,broad s); 7.5–6.8 (4H,m); 7.0 (4H,dofd); 4.75 (1H, q); 4.2 (2H,q); 1.6 (3H,d); 1.2 (3H,t). |
| 22 | 1 | 8.9 (1H,broad s); 8.4 (1H,s); 7.7–7.4 (3H,m); 7.1 (4H,s); 4.8 (1H,q); 4.25 (2H,q); 1.65 (3H,d); 1.3 (3H,t). |
| 23 | 20 | 8.4 (1H,broad s); 7.8 (1H, broad s); 7.5–7.0 (3H,m); 6.9 (4H,dofd); 4.7 (1H,q); 4.2 (2H,q); 3.25 (3H,s); 1.6 (3H,d); 1.25 (3H,t). |
| 25 | 2 | 8.51 (1H,broad s); 8.15 (1H,d); 7.6–6.8 (3H,m); 7.0 (4H,dofd); 4.8 (1H,q); 3.8 (3H,s); 3.3 (3H,s); 1.65 (3H,d). |
| 27 | 15 | 8.27 (1H,broad s); 7.67 (2H, broad s); 7.35 (1H,s); 7.03 (4H,dofd); 4.78 (1H,q); 4.26(2H,q); 1.68 (3H,d); 1.29 (3H,t). |
| 28 | 2 | 8.64 (1H,broad s); 8.42 (1H,d); 7.6–7.0 (3H,m); 7.0 (4H,dofd); 4.75 (1H,q); 4.25 (2H,q); 1.65 (3H,d); 1.25 (3H,t). |
| 29 | 15 | 7.9 (1H,broad s); 7.4–7.2 (2H,m); 7.12 (1H,s); 7.00 (4H,dofd); 4.76 (1H,q); 4.25 (2H,q); 1.64 (3H,d); 1.28 (3H,t). |
| 30 | 19 | 8.64 (1H,d); 8.23 (1H,s); 7.7–7.4 (3H,m); 7.1 (4H,dofd); 6.15 (1H,s); 4.75 (1H,q); 4.25 (2H,q); 1.64 (3H,d); 1.25 (3H,t). |
| 31 | 10 | 8.5 (1H,d); 8.28 (1H,s); 8.1–7.8 (2H,m); 7.12 (4H,dofd); 4.9 (1H,q); 4.2 (1H,q); 1.6 (3H,d); 1.2 (3H,t)+. |
| 32 | 20 | 8.58 (1H,d); 8.22 (1H,s); 7.7–7.2 (3H,m); 7.05 (4H,dofd); 4.8 (1H,q); 4.2 (1H,q); 3.4 (3H,s); 1.6 (3H,d); |

TABLE 3-continued

| Compound No | Method of Example | Proton Magnetic Resonance Spectrum Chemical Shift δ in ppm |
|---|---|---|
| 33 | 11 | 1.2 (3H,t).<br>8.60 (1H,d); 8.2–8.0 (2H,m); 7.6 (1H,dofd); 6.93 (4H,broad s); 4.70 (1H,q); 4.25 (2H,q); 1.60 (3H,d); 1.26 (3H,t). |
| 34 | 11 | 8.15–8.0 (2H,m); 7.6 (1H,dofd); 6.84 (4H,dofd); 4.71 (1H,q); 4.25 (2H,q); 1.64 (3H,d); 1.24 (3H,t). |
| 35 | 14 | 8.88 (1H,d); 8.36 (1H,s); 7.8–7.4 (3H,m); 7.00 (4H,dofd); 4.25 (2H,q); 1.63 (6H,s); 1.29 (3H,t). |
| 36 | 2 | 8.75 (1H,s); 8.15 (1H,d); 7.7–7.5 (2H,m); 7.00 (4H,dofd); 6.8 (1H, broad s); 4.75 (1H,q); 4.25 (2H,q); 3.3 (3H,s); 1.62 (3H,d); 1.25 (3H,t). |
| 37 | 22 | 8.76 (1H,d); 8.05 (1H,s); 7.55–7.3 (3H,m); 7.00 (4H,dofd); 4.79 (1H,q); 4.19 (2H,t); 1.61 (3H,d); 1.6–0.9 (7H,m). |
| 38 | 22 | 8.77 (1H,d); 8.04 (1H,s); 7.6–7.3 (3H,m); 6.99 (4H,dofd); 4.77 (1H,q); 4.15 (2H,t); 1.68 (3H,d); 1.6–0.9 (5H,m). |
| 39 | 23 | 8.82 (1H,d); 8.1–7.5 (4H,m); 7.3 (2H, broad s); 7.1 (4H,dofd); 4.65 (1H,q); 1.46 (3H,d). |
| 40 | 1 | 8.65 (1H,d); 7.8–7.0 (4H,m); 7.0 (4H, dofd); 4.63 (1H,q); 4.20 (2H,q); 1.52 (3H,d); 1.15 (3H,t). |

EXAMPLE 27

Concentrated formulations of the compounds of the invention were prepared by:

(a) in the case of oils and waxy solids, dissolving the compound in toluene containing 7% v/v "Teric" N13 ("Teric" is a Trade Mark and "Teric" N13, a product of ethoxylation of nonylphenol, is available from ICI Australia Limited) and 3% v/v "Kemmat" SC15B is a formulation of calcium dodecylbenzene sulfonate); or (b) in the case of crystalline solids, adding 5 parts by weight of the compound and 1 part by weight of "Dyapol" PT ("Dyapol" is a Trade Mark and "Dyapol" PT is an anionic suspending agent) to 94 parts by weight of an aqueous solution containing 0.25% v/v of "Teric" N8 (a product of ethoxylation of nonylphenol) and ball-milling the mixture to produce a stable suspension. The emulsifiable concentrates and suspensions were then diluted with water to give an aqueous composition of the required concentration suitable for use in the evaluation of pre-emergence and post-emergence herbicidal activity of the compounds of the invention.

EXAMPLE 28

The pre-emergent herbicidal activity of the compounds of the invention formulated as described in Example 27 was assessed by the following procedure.

The seeds of the test species were sown in rows 2 cm deep in soil contained in seed boxes. The monocotyledonous plants and the dicotyledonous plants were sown in separate boxes and after sowing the two boxes were sprayed with the required quantity of a composition of the invention. Two duplicate seed boxes were prepared in the same manner but were not sprayed with a composition of the invention and were used for comparison purposes. All the boxes were placed in a glasshouse, lightly watered with an overhead spray to initiate germination and then sub-irrigated as required for optimum plant growth. After three weeks the boxes were removed from the glasshouse and the effect of the treatment was visually assessed. The results are presented in Table 4 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (—) means that no experiment is carried out.

The names of the test plants are as follows:

| | |
|---|---|
| Wh | Wheat |
| Ot | Wild Oats |
| Rg | Ryegrass |
| Jm | Japanese millet |
| P | Peas |
| Ip | Ipomea |
| Ms | Mustard |
| Sf | Sunflower |

TABLE 4

PRE-EMERGENCE HERBICIDAL ACTIVITY

| Compound No | Application Rate kg/ha | Test Plant | | | | | | | |
|---|---|---|---|---|---|---|---|---|---|
| | | Wh | Ot | Rg | Jm | P | Ip | Ms | Sf |
| 1 | 5 | 1 | 0 | 5 | 5 | 0 | 0 | 0 | 0 |
| 1 | 1 | 0 | 0 | 5 | 4 | 0 | 0 | 0 | 0 |
| 1 | 0.5 | 0 | 0 | 4 | 4 | 0 | 0 | 0 | 0 |
| 4 | 5 | 0 | 1 | 5 | 5 | 0 | 0 | 0 | 0 |
| 5 | 5 | 4 | 3 | 5 | 5 | 0 | 0 | 0 | 0 |
| 5 | 1 | 0 | 0 | 3 | 3 | 0 | 0 | 0 | 0 |
| 5 | 0.5 | 0 | 0 | 2 | 4 | 0 | 0 | 0 | 0 |
| 5 | 0.25 | 0 | 0 | 0 | 0 | 0 | 0 | 0 | 0 |
| 15 | 5 | 2 | 0 | 4 | 5 | 0 | 0 | 0 | 0 |
| 15 | 1 | 0 | 0 | 0 | 0 | 0 | 0 | 0 | 0 |
| 15 | 0.5 | 0 | 2 | 3 | 0 | 0 | 0 | 0 | 0 |
| 16 | 5.0 | 0 | 0 | 4 | 4 | 0 | 0 | 0 | 0 |
| 22 | 5.0 | 3 | 5 | 5 | 5 | 0 | 0 | 0 | 0 |
| 22 | 1.0 | 1 | 4 | 3 | 5 | 0 | 0 | 0 | 0 |
| 22 | 0.5 | 0 | 1 | 4 | 4 | 0 | 0 | 0 | 0 |
| 26 | 5.0 | 0 | 0 | 3 | 4 | 0 | 0 | 0 | 0 |
| 28 | 5.0 | 3 | 1 | 5 | 5 | 0 | 0 | 0 | 0 |
| 35 | 5.0 | 0 | 2 | 3 | 4 | 0 | 0 | 0 | 0 |
| 39 | 5.0 | 4 | 4 | 5 | 5 | 0 | 0 | 0 | 0 |
| 39 | 1.0 | 3 | 0 | 5 | 5 | 0 | 0 | 0 | 0 |
| 40 | 5.0 | 5 | 5 | 5 | 5 | 0 | 0 | 0 | 0 |
| 40 | 1.0 | 4 | 3 | 5 | 5 | 0 | 0 | 0 | 0 |
| 45 | 5.0 | 0 | 3 | 4 | 5 | 0 | 0 | 0 | 0 |

EXAMPLE 29

The post-emergent herbicidal activity of the compounds of the invention formulated as described in Example 27 was assessed by the following procedure.

The seeds of the test species were sown in rows 2 cm deep in soil contained in seed boxes. The monocotyledonous plants and the dioctyledonous plants were sown in separate seed boxes in duplicate. The four seed boxes were placed in a glasshouse, lightly watered with an overhead spray to initiate germination and then sub-irrigated as required for optimum plant growth. After the plants had grown to a height of about 10 to 12.5 cm one box of each of the monocotyledonous plants and the dioctyledonous plants was removed from the glasshouse and sprayed with the required quantity of a composition of the invention. After spraying the boxes were returned to the glasshouse for a further 3 weeks and the effect of treatment was visually assessed by comparison with the untreated controls. The results are presented in Table 5 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (—) means that no experiment was carried out.

The names of the test plants are as follows:

| | |
|---|---|
| Wh | Wheat |
| Ot | Wild Oats |
| Rg | Ryegrass |
| Jm | Japanese millet |
| P | Peas |
| Ip | Ipomea |
| Ms | Mustard |
| Sf | Sunflower |

TABLE 5

POST-EMERGENCE HERBICIDAL ACTIVITY

| Compound No | Application Rate kg/ha | Wh | Ot | Rg | Jm | P | Ip | Ms | Sf |
|---|---|---|---|---|---|---|---|---|---|
| 1 | 5 | 5 | 0 | 5 | 5 | 0 | 5 | 3 | 3 |
| 1 | 1 | 3 | 0 | 5 | 5 | 0 | 0 | 0 | 0 |
| 1 | 0.5 | 1 | 0 | 3 | 5 | 0 | 0 | 0 | 0 |
| 4 | 5 | 4 | 0 | 5 | 5 | 0 | 1 | 0 | 1 |
| 5 | 5 | 5 | 5 | 5 | 5 | 0 | 4 | 4 | 2 |
| 5 | 1 | 5 | 5 | 4 | 5 | 0 | 0 | 0 | 0 |
| 5 | 0.5 | 5 | 5 | 5 | 5 | 0 | 0 | 0 | 0 |
| 5 | 0.25 | 5 | 5 | 5 | 5 | 0 | 0 | 0 | 0 |
| 5 | 0.1 | 5 | 4 | 4 | 5 | 0 | 0 | 0 | 0 |
| 15 | 5 | 5 | 4 | 5 | 5 | 0 | 0 | 0 | 0 |
| 15 | 1 | 5 | 0 | 4 | 5 | 0 | 0 | 0 | 0 |
| 15 | 0.5 | 5 | 0 | 0 | 5 | 0 | 0 | 0 | 0 |
| 16 | 5.0 | 3 | 2 | 3 | 4 | 0 | 0 | 5 | 0 |
| 22 | 5.0 | 5 | 5 | 5 | 5 | 0 | 0 | 2 | 0 |
| 22 | 1.0 | 5 | 5 | 5 | 5 | 0 | 2 | 2 | 0 |
| 22 | 0.05 | 3 | 4 | 4 | 5 | 0 | 0 | 0 | 0 |
| 26 | 5.0 | 4 | 4 | 5 | 5 | 0 | 0 | 3 | 2 |
| 28 | 5.0 | 5 | 5 | 5 | 5 | 0 | 3 | 0 | 3 |
| 28 | 1.0 | 5 | 5 | 5 | 5 | 0 | 0 | 0 | 0 |
| 35 | 5.0 | 5 | 5 | 3 | 5 | 0 | 0 | 0 | 0 |
| 39 | 5.0 | 5 | 5 | 5 | 5 | 1 | 5 | 0 | 0 |
| 39 | 1.0 | 4 | 4 | 4 | 5 | 0 | 0 | 0 | 0 |
| 40 | 5.0 | 5 | 5 | 5 | 5 | 0 | 5 | 2 | 3 |
| 40 | 1.0 | 5 | 5 | 5 | 5 | 0 | 5 | 1 | 1 |
| 45 | 5.0 | 5 | 5 | 5 | 5 | 0 | 0 | 0 | 0 |

EXAMPLE 30

The compounds were formulated for test by mixing an appropriate amount with 5 ml of an emulsion prepared by diluting 160 ml of a solution containing 21.8 g per liter of "Span" 80 and 78.2 g per liter of "Tween" 20 in methylcyclohexanone to 500 ml with water. "Span" 80 is a Trade Mark for a surface-active agent comprising sorbitan monolaurate. "Tween" 20 is a Trade Mark for a surface-active agent comprising a condensate of sorbitan monolaurate with 20 molar proportions of ethylene oxide. Each 5 ml emulsion containing a test compound was then diluted to 40 ml with water and sprayed on to young pot plants (post-emergence test) of the species named in Table 6 below. Damage to test plants was assessed after 14 days on a scale of 0 to 5 where 0 is 0 to 20% damage and 5 is complete kill. In a test for pre-emergence herbicidal activity, seeds of the test plants were sown in a shallow slit formed in the surface of soil in fibre trays. The surface was then levelled and sprayed, and fresh soil then spread thinly over the sprayed surface. Assessment of herbicidal damage was carried out after 21 days using the same scale of 0 to 5 as the post-emergence test. In both cases the degree of herbicidal damage was assessed by comparison with untreated control plants. The results are given in Table 6 below. A dash (—) means that no experiment was carried out.

TABLE 6

PART A

| Compound No | APPLICATION Method | Rate (kg/ha) | Sb | Rp | Ct | Sy | Mz | Ww | Rc | Sn | Ip | Am | Pi | Ca |
|---|---|---|---|---|---|---|---|---|---|---|---|---|---|---|
| 2 | PRE | 2.0 | 0 | 0 | 0 | 0 | 2 | 2 | 3 | 1 | 0 | 0 | 0 | 0 |
| 2 | PRE | 0.5 | 0 | 0 | 1 | 0 | 1 | 1 | 0 | 0 | 1 | — | 0 | — |
| 2 | POST | 2.0 | 1 | 0 | 0 | 0 | 5 | 0 | 2 | 0 | 0 | 0 | — | 1 |
| 2 | POST | 0.5 | 0 | 0 | 0 | 0 | 3 | 0 | 0 | 0 | 0 | 0 | — | 0 |
| 5 | PRE | 2.0 | 0 | 0 | 1 | 0 | 4 | 5 | 5 | 1 | 1 | — | 0 | — |
| 5 | PRE | 0.5 | 0 | 0 | 0 | 0 | 2 | 4 | 5 | 1 | 1 | — | 1 | — |
| 5 | PRE | 0.05 | — | — | — | — | 0 | 2 | 1 | — | — | — | — | — |
| 5 | PRE | 0.025 | — | — | — | — | 0 | 1 | — | — | — | — | — | — |
| 5 | POST | 2.0 | 1 | — | 1 | 1 | 5 | 4 | 4 | 3 | 0 | — | 0 | 1 |
| 5 | POST | 0.5 | 2 | — | 1 | 1 | 5 | 4 | 4 | 1 | 0 | — | 0 | 0 |
| 5 | POST | 0.05 | — | — | — | — | 4 | 4 | 2 | — | — | — | — | — |
| 5 | POST | 0.025 | — | — | — | — | 4 | 4 | 2 | — | — | — | — | — |
| 15 | PRE | 2.0 | 0 | 1 | 0 | 0 | 0 | 3 | 0 | 1 | 0 | — | — | 1 |
| 15 | PRE | 0.5 | 0 | 0 | 0 | 0 | 0 | 2 | 0 | 0 | 0 | — | — | 0 |
| 15 | POST | 2.0 | 1 | 0 | 0 | — | 4 | 4 | 0 | 0 | 0 | — | 0 | 0 |
| 15 | POST | 0.5 | 0 | 0 | 0 | 3 | 3 | 4 | 0 | 0 | 0 | — | 0 | 0 |
| 22 | PRE | 0.2 | — | — | — | — | 0 | 2 | 0 | — | — | — | — | — |
| 22 | POST | 0.2 | — | — | — | — | — | — | — | 4 | 3 | 0 | — | — |
| 23 | PRE | 2.0 | — | — | — | — | 0 | 0 | 0 | — | — | — | — | — |
| 23 | POST | 2.0 | — | — | — | — | 4 | 0 | 0 | — | — | — | — | — |
| 28 | Pre | 0.2 | — | — | — | — | 0 | 3 | 2 | — | — | — | — | — |
| 28 | POST | 0.2 | — | — | — | — | 2 | 2 | 0 | — | — | — | — | — |

PART B

| Compound | APPLICATION Method Rate | TEST PLANT |
|---|---|---|

TABLE 6-continued

| No | | (kg/ha) | Ga | Xa | Ab | Cv | Av | Dg | Al | St | Ec | Sh | Ag | Cn |
|---|---|---|---|---|---|---|---|---|---|---|---|---|---|---|
| 2 | PRE | 2.0 | — | — | 0 | 0 | 0 | 3 | 2 | 0 | 4 | 3 | 4 | 0 |
| 2 | PRE | 0.5 | — | — | 0 | — | 0 | 0 | 0 | 0 | 3 | 2 | 1 | 0 |
| 2 | POST | 2.0 | 0 | 0 | 1 | 1 | 0 | 1 | 3 | 1 | 5 | 4 | 0 | 0 |
| 2 | POST | 0.5 | 0 | 0 | 0 | 0 | 1 | 0 | 1 | 0 | 3 | 3 | 0 | 0 |
| 5 | PRE | 2.0 | 0 | 0 | 0 | 1 | 3 | 5 | 5 | 5 | 5 | 4 | 5 | 0 |
| 5 | PRE | 0.5 | 0 | 0 | 0 | 0 | 2 | 4 | 5 | 5 | 5 | 3 | 5 | 0 |
| 5 | PRE | 0.05 | — | — | — | — | 2 | 0 | 1 | 0 | 0 | 0 | 5 | 0 |
| 5 | PRE | 0.025 | — | — | — | — | — | 1 | 0 | 0 | 0 | 0 | — | 0 |
| 5 | POST | 2.0 | 1 | 1 | 1 | 1 | 4 | 5 | 4 | 5 | 5 | 5 | 5 | 2 |
| 5 | POST | 0.5 | 0 | 0 | 0 | 1 | 4 | 5 | 4 | 5 | 5 | 5 | 5 | 2 |
| 5 | POST | 0.05 | 0 | 0 | 0 | 0 | 4 | 4 | 4 | 4 | 5 | 5 | 3 | 0 |
| 5 | POST | 0.025 | — | — | — | — | 4 | 3 | 4 | 5 | 5 | 4 | 4 | 0 |
| 15 | PRE | 2.0 | 0 | 0 | 0 | 0 | 1 | 3 | 2 | 2 | 1 | 1 | 5 | 0 |
| 15 | PRE | 0.5 | 0 | 0 | 0 | 0 | 0 | 0 | 0 | 0 | 0 | 0 | 0 | 0 |
| 15 | POST | 2.0 | 0 | 0 | 0 | 0 | 1 | 4 | 4 | 4 | 4 | 4 | 3 | 0 |
| 15 | POST | 0.5 | 0 | 0 | 1 | 0 | 1 | 3 | 3 | 4 | 4 | 3 | 2 | 0 |
| 22 | PRE | 0.2 | — | — | — | — | 2 | 0 | 0 | 0 | 0 | 2 | 5 | 0 |
| 22 | POST | 0.2 | — | — | — | — | 4 | 4 | 4 | 5 | 4 | 5 | 3 | 0 |
| 23 | PRE | 2.0 | — | — | — | — | 1 | 0 | 0 | 0 | 0 | 0 | 2 | 1 |
| 23 | POST | 2.0 | — | — | — | — | 0 | 1 | 1 | 2 | 1 | 4 | 0 | 0 |
| 28 | PRE | 0.2 | — | — | — | — | 2 | 0 | 3 | 0 | 0 | 0 | 2 | 0 |
| 28 | POST | 0.2 | — | — | — | — | 1 | 1 | 2 | 0 | 2 | 2 | 2 | 0 |

The names of the test plants were as follows:

| Sb | Sugar beet |
| Rp | Rape |
| Ct | Cotton |
| Sy | Soy bean |
| Mz | Maize |
| Ww | Winter wheat |
| Rc | Rice |
| Sn | *Senico vulgaris* |
| Ip | *Ipomea purpurea* |
| Am | *Amaranthus retroflexus* |
| Pi | *Polygonum aviculare* |
| Ca | *Chenopodium album* |
| Ga | *Galium aparine* |
| Xa | *Xanthium pensylvanicum* |
| Ab | *Abutilon theophrasti* |
| Cv | *Convolvulus arvensis* |
| Av | *Avena futua* |
| Dg | *Digitaria sanguinalis* |
| Al | *Alopecurus myosuroides* |
| St | *Setaria viridis* |
| Ec | *Echinochloa crus-galli* |
| Sh | *Sorghum halepense* |
| Ag | *Agropyron repens* |
| Cn | *Cyperus rotundas* |

What is claimed is:

1. A compound of the formula:

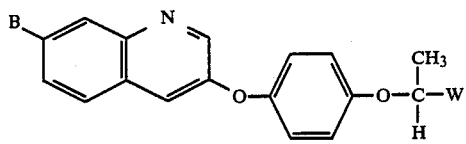

where B is chlorine or fluorine and W represents the group

wherein G is hydroxy, $C_1$ to $C_6$ alkoxy, $C_2$ to $C_6$ alkenyloxy, $C_2$ to $C_6$ alkynyloxy and the group OM wherein M is an alkali metal or alkaline earth metal ion.

2. A compound according to claim 1 wherein G is selected from methoxy, ethoxy, n-propoxy and n-butoxy.

3. A compound selected from ethyl 2-{4-[(7-chloroquinolin-3-yl)oxy}phenoxy-propionate and ethyl 2-{4-[(7-fluoroquinolin-3-yl)oxy]phenoxy}propionate.

4. A compound of the formula:

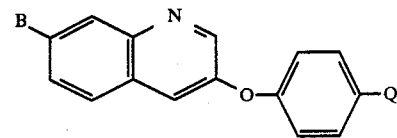

where B is chlorine or fluorine and Q is hydroxy or $C_1$ to $C_6$ alkoxy.

5. A herbicidal composition comprising as active ingredient a compound as defined according to claim 1 and a carrier therefor.

6. A process for severely damaging or killing unwanted plants which process comprises applying to said plants, or to the growth medium of said plants, an effective amount of a compound as defined according to claim 1.

7. A process for selectively controlling the growth of monocotyledonous weeds in dicotyledonous crops which process comprises applying to said crop, or to the growth medium of said crop, a compound as defined according to claim 1 in an amount sufficient to severely damage or kill the weeds but insufficient to substantially damage the crop.

8. A process according to claim 6 wherein the compound is applied at a rate in the range from 0.005 to 20 kilograms per hectare.

9. A process according to claim 7 wherein the compound is applied at a rate in the range from 0.005 to 20 kilograms per hectare.

* * * * *